(12) United States Patent
Case et al.

(10) Patent No.: US 7,458,987 B2
(45) Date of Patent: Dec. 2, 2008

(54) VASCULAR VALVES HAVING IMPLANTED AND TARGET CONFIGURATIONS AND METHODS OF PREPARING THE SAME

(75) Inventors: Brian C. Case, Bloomington, IN (US); Jacob A. Flagle, Indianapolis, IN (US); Michael L. Garrison, Indianapolis, IN (US); F. Joseph Obermiller, West Lafayette, IN (US); Dusan Pavcnik, Portland, OR (US)

(73) Assignee: Cook Incorporated, Bloomington, IN (US)

( * ) Notice: Subject to any disclaimer, the term of this patent is extended or adjusted under 35 U.S.C. 154(b) by 292 days.

(21) Appl. No.: 11/260,770

(22) Filed: Oct. 27, 2005

(65) Prior Publication Data

US 2006/0212111 A1 Sep. 21, 2006

Related U.S. Application Data

(60) Provisional application No. 60/623,460, filed on Oct. 29, 2004.

(51) Int. Cl.
*A61F 2/06* (2006.01)

(52) U.S. Cl. .................... 623/1.24; 623/2.38

(58) Field of Classification Search ....... 623/1.24–1.26, 623/1.42, 2.13–2.19
See application file for complete search history.

(56) References Cited

U.S. PATENT DOCUMENTS

| | | | |
|---|---|---|---|
| 4,218,782 A | 8/1980 | Rygg | |
| 4,902,508 A | 2/1990 | Badylak et al. | |
| 5,156,620 A | 10/1992 | Pigott | |
| 5,411,552 A | 5/1995 | Andersen et al. | |
| 5,554,389 A | 9/1996 | Badylak et al. | |
| 5,607,465 A | 3/1997 | Camilli | |
| 5,616,608 A | 4/1997 | Kinsella et al. | |
| 5,855,601 A * | 1/1999 | Bessler et al. | 623/2.38 |
| 5,993,844 A | 11/1999 | Abraham et al. | |
| 6,099,567 A | 8/2000 | Badylak et al. | |
| 6,110,201 A | 8/2000 | Quijano et al. | |
| 6,126,686 A * | 10/2000 | Badylak et al. | 623/1.24 |
| 6,168,614 B1 | 1/2001 | Andersen et al. | |
| 6,200,336 B1 | 3/2001 | Pavcnik et al. | |
| 6,206,931 B1 | 3/2001 | Cook et al. | |
| 6,287,334 B1 | 9/2001 | Moll et al. | |
| 6,299,637 B1 | 10/2001 | Shaolian et al. | |
| 6,508,833 B2 | 1/2003 | Pavcnik et al. | |
| 6,582,462 B1 | 6/2003 | Andersen et al. | |
| 6,716,241 B2 | 4/2004 | Wilder et al. | |
| 6,752,828 B2 | 6/2004 | Thornton | |
| 2001/0011187 A1 | 8/2001 | Pavcnik et al. | |

(Continued)

FOREIGN PATENT DOCUMENTS

WO    WO 01/19285    3/2001

(Continued)

*Primary Examiner*—Suzette J Gherbi
(74) *Attorney, Agent, or Firm*—Woodard, Emhardt, Moriarty, McNett & Henry LLP

(57) ABSTRACT

Described are vascular valve devices for implantation in a patient. The vascular valve devices are designed to compensate for the retraction characteristics of a remodelable material used to form one or more leaflets. Alternatively, or in addition, the devices are designed to reduce retraction of the remodelable leaflet-forming material. Further described are methods for preparing and using these vascular valve devices.

33 Claims, 9 Drawing Sheets

U.S. PATENT DOCUMENTS

| | | |
|---|---|---|
| 2001/0039450 A1 | 11/2001 | Pavcnik et al. |
| 2002/0123800 A1 | 9/2002 | Taheri et al. |
| 2002/0188348 A1 | 12/2002 | DiMatteo et al. |
| 2003/0036795 A1 | 2/2003 | Andersen et al. |
| 2003/0078659 A1* | 4/2003 | Yang ................. 623/13.17 |
| 2003/0130726 A1 | 7/2003 | Thorpe |
| 2003/0191525 A1 | 10/2003 | Thornton |
| 2003/0208261 A1 | 11/2003 | Thorpe et al. |
| 2004/0015230 A1 | 1/2004 | Moll et al. |
| 2004/0049262 A1 | 3/2004 | Obermiller et al. |
| 2004/0186558 A1 | 9/2004 | Pavcnik et al. |
| 2004/0193253 A1 | 9/2004 | Thorpe et al. |
| 2004/0260389 A1 | 12/2004 | Case et al. |
| 2005/0182483 A1* | 8/2005 | Osborne et al. ............ 623/1.24 |
| 2007/0038295 A1* | 2/2007 | Case et al. ................. 623/2.18 |

FOREIGN PATENT DOCUMENTS

| | | |
|---|---|---|
| WO | WO 03/070124 | 8/2003 |

* cited by examiner

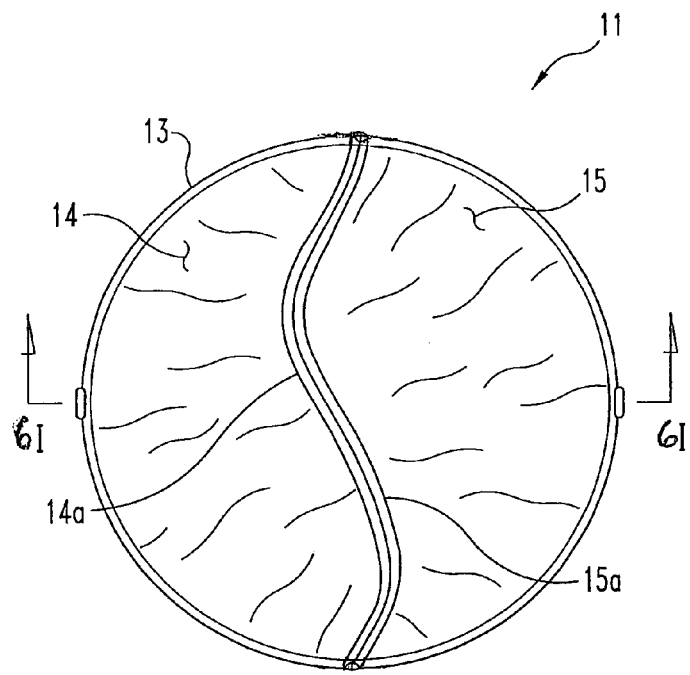
Fig. 4I^c
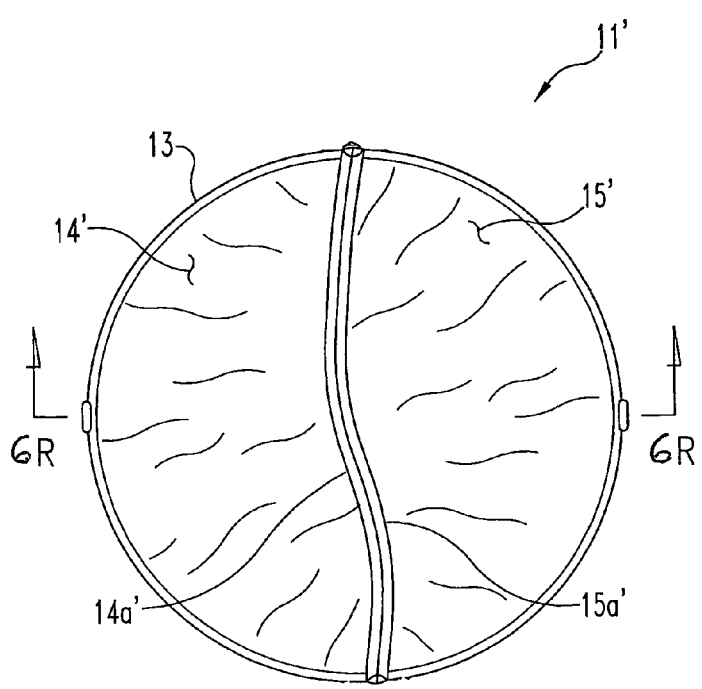
Fig. 4R^c

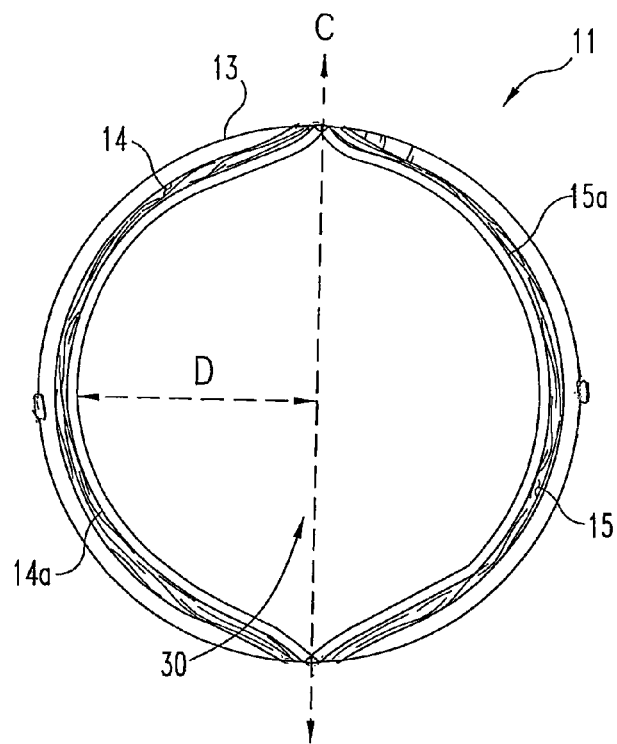
*Fig. 5I°*
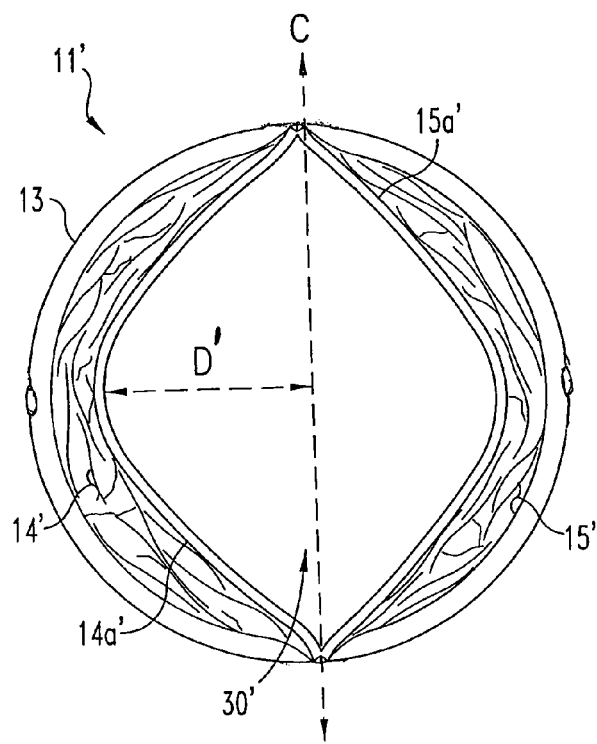
*Fig. 5R°*

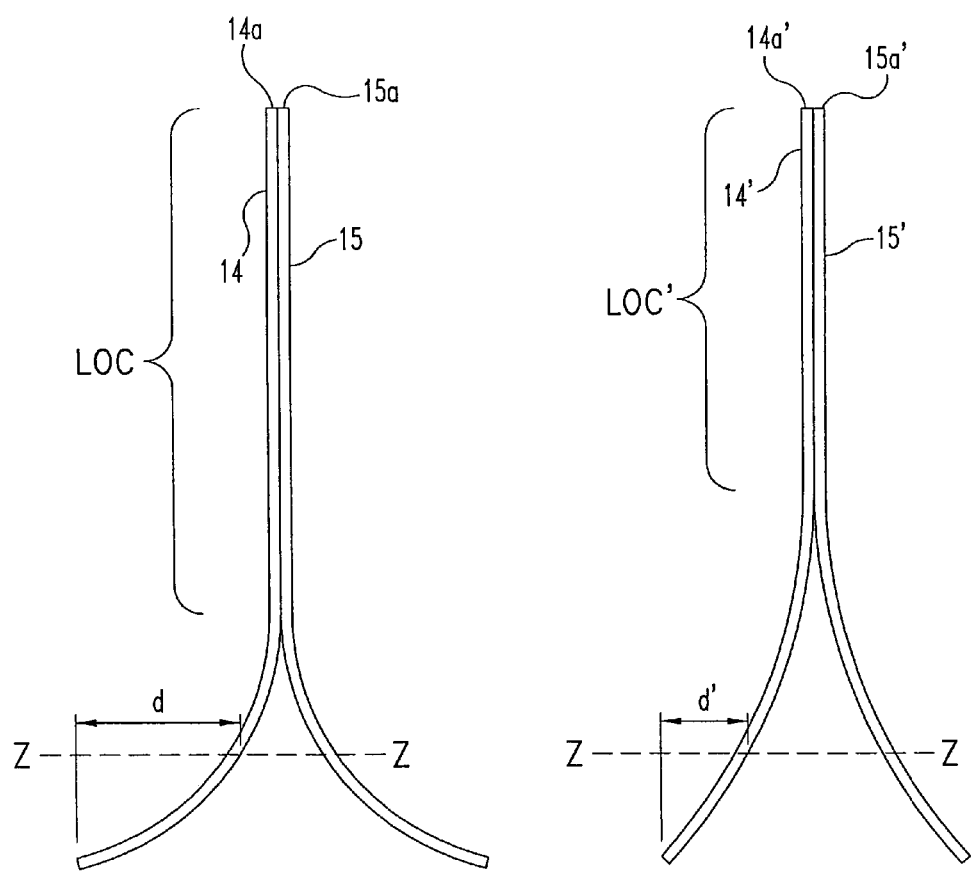
Fig. 6I<sup>c</sup>　　　　Fig. 6R<sup>c</sup>

VASCULAR VALVES HAVING IMPLANTED AND TARGET CONFIGURATIONS AND METHODS OF PREPARING THE SAME

STATEMENT OF RELATED APPLICATIONS

This application claims the benefit of priority of U.S. Provisional Patent Application Ser. No. 60/623,460 filed Oct. 29, 2004 which is incorporated herein by reference in its entirety.

TECHNICAL FIELD OF THE INVENTION

The present invention resides generally in the field of medical devices and, more particularly, relates to medical valves such as those for implantation within the vascular system.

BACKGROUND OF THE INVENTION

In all vertebrates, blood is transported away from the heart and throughout the body via arteries and returns to the heart through veins. To allow for optimal transport back to the heart and to reduce blood pressure build-up, veins contain various valves within their lumens, which open to permit blood flow to the heart but close to prevent the backflow of blood Problems can arise when these venous valves fail to function properly. For example, venous valves can become incompetent or damaged by disease such that the backflow of blood is not prevented. When this occurs, blood pressure builds up and the veins and their valves become dilated, particularly in the lower extremities. If enough pressure builds, the condition of venous insufficiency may develop. The severity of this condition is substantial, resulting in swelling, extensive pain, deformities and, in the most severe cases, the development of ulcers can occur. If these ulcers become infected, amputation may ultimately be necessary.

Currently, initial treatments for venous insufficiency include elevation of the legs or the use of compression stockings. If surgery is determined to be necessary, vein stripping is often performed, which involves the removal of the incompetent or damaged vein(s).

The development of artificial and biological valves has also been suggested to return normal pressure to the veins. There are a variety of these valves described in the art, which are generally designed to allow normal flow of blood back to the heart, while restricting retrograde flow. For example, U.S. Pat. No. 6,508,833 discloses in one specific embodiment a multiple-sided medical device comprising a closed frame of a single piece of wire or other resilient material and having a series of bends and interconnecting sides. The device has both a flat configuration and a second, folded configuration that comprises a self-expanding stent. The stent can be pushed from a delivery catheter into the lumen of a duct or vessel. A covering of fabric or other flexible material is sutured or attached to the frame to form an artificial valve. The flexible material utilized in these valves can be comprised of submucosal tissue obtained from various animals, such as, for example, pigs, cattle, and sheep. The preparation of submucosal tissue is generally described in U.S. Pat. Nos. 4,902, 508, 5,554,389 and 6,206,931.

In view of the background in this area, there remain needs for improved and/or alternative valve devices and methods for modifying blood flow within vascular vessels. The present invention is addressed to these needs.

SUMMARY OF THE INVENTION

In one aspect, the present invention provides a vascular valve device for implantation in a patient to form one or more leaflets in a target configuration. The valve device includes a frame; and a retractable covering material attached to the frame in a first configuration for implantation, the first configuration having one or more leaflet-forming portions formed from the retractable covering material and including an adaptation to account for retraction of the covering material.

In another embodiment, the invention provides a vascular valve device for implantation in a patient to form one or more leaflets of the patient's tissue in a target valve configuration. The valve device comprises a frame element and a remodelable covering that undergoes retraction during the remodeling process. The remodelable covering is attached to the frame element in a first configuration for implantation, and includes one or more leaflet-forming portions formed from the remodelable covering. The first configuration is adapted wherein upon remodeling of the one or more leaflet-forming portions with the patient's tissue and consequent retraction, one or more corresponding leaflets comprising tissue of the patient are formed in the target valve configuration.

In another embodiment, the invention provides a vascular valve device for implantation in a patient to form one or more leaflets of the patient's tissue in a target configuration, wherein a leaflet-forming remodelable material has been treated to reduce retraction upon remodeling. In one aspect, the valve device comprises a frame and a remodelable covering comprised of a remodelable scaffold and at least one agent that reduces retraction of the covering upon remodeling. The remodelable covering is attached to the frame and provides one or more leaflets. Upon implantation of the device and remodeling of the covering with the patient's tissue, one or more leaflets in the target valve configuration are formed.

Methods for preparing the aforementioned vascular valve devices also are provided. A first method comprises providing a frame element, forming a first configuration for implantation by attaching to the frame element a remodelable covering that retracts upon remodeling, the first configuration having one or more leaflet-forming portions from the remodelable covering. The first configuration for implantation is adapted wherein upon remodeling of the one or more leaflet-forming portions and consequent retraction, one or more corresponding leaflets comprised of the patient's tissue in a target configuration are formed.

Another method for preparing a valve device of the invention comprises forming a retraction-reduced remodelable material into one or more valve leaflets. In one embodiment, the method includes providing a frame element, and attaching to the frame element a remodelable covering comprised of a remodelable scaffold and at least one agent that reduces retraction of the covering upon remodeling. The covering provides one or more leaflets. Upon implantation of the device and remodeling of the covering with the patient's tissue, one or more leaflets in a target valve configuration are formed.

In another aspect, the invention provides a vascular valve device for implantation in a patient to form one or more leaflets in a target configuration that includes a frame and a retractable covering. The retractable covering is attached to the frame in a first implantation configuration that has one or more leaflet-forming portions formed from the retractable covering and that includes an adaptation to account for retraction of the covering.

In yet another aspect, the invention provides illustrative vascular valve devices, as discussed herein, enclosed in sterile medical packaging.

Additional embodiments as well as features and advantages of the invention will be apparent to those skilled in the art from the descriptions herein.

BRIEF DESCRIPTION OF THE DRAWINGS

FIGS. 4I$^c$ and 4R$^c$ provide overhead views of an illustrative vascular valve device such as that depicted in FIG. 1 in a closed position in the implanted (non-remodeled) and remodeled configurations, respectively.

FIGS. 5I$^o$ and 5R$^o$ provide overhead views of an illustrative vascular valve device such as that depicted in FIG. 1 in an open position in the implanted (non-remodeled) and remodeled configurations, respectively.

FIGS. 6I$^c$ and 6R$^c$ provide a cross-sectional views of the leaflets of the illustrative devices depicted in FIGS. 4I$^c$ and 4R$^c$ taken along lines 6I-6I and 6R-6R respectively and viewed in the direction of the arrows.

DETAILED DESCRIPTION

Figure 1:
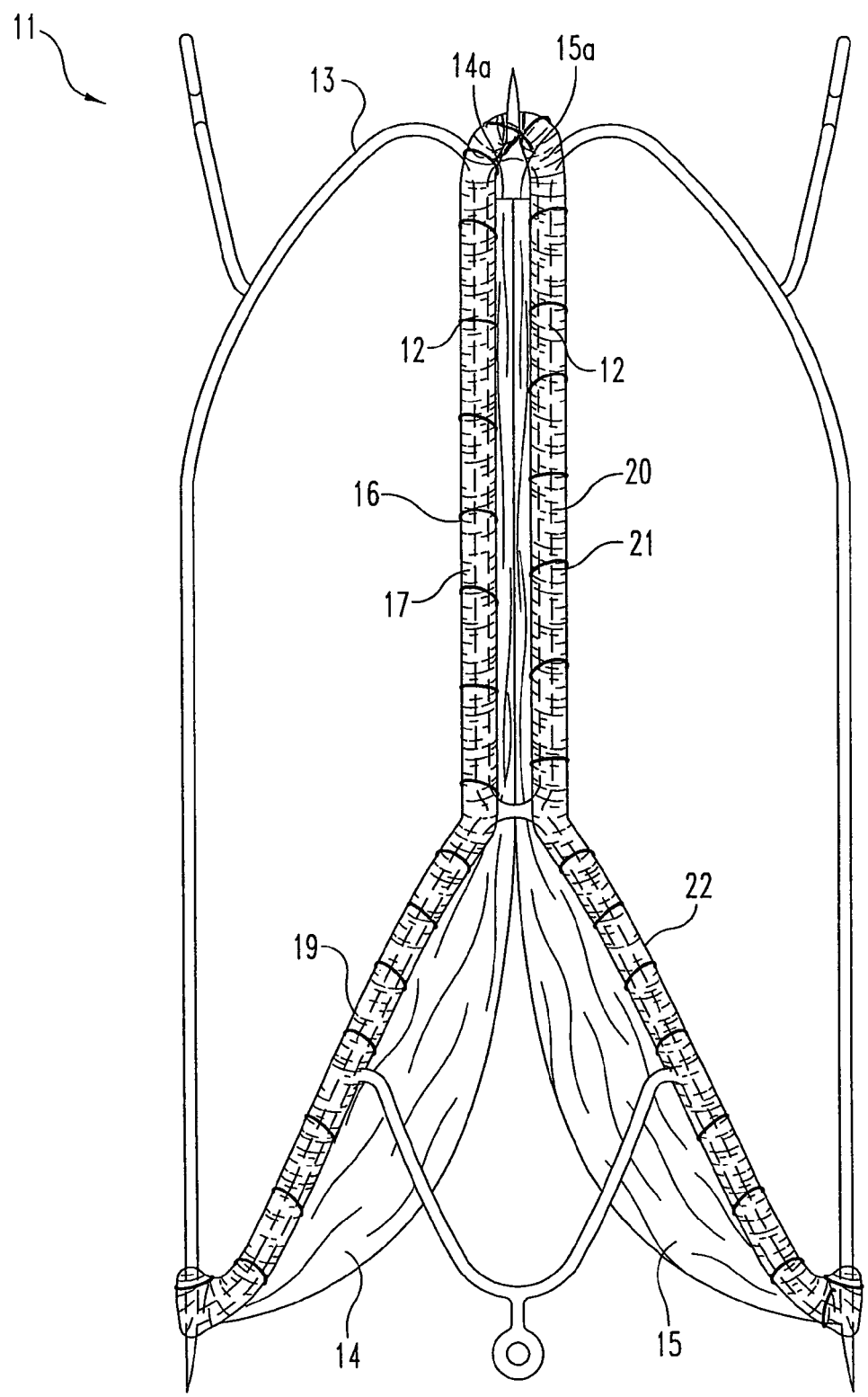
FIG. 1 provides a side view of an illustrative vascular valve device that includes a remodelable covering material attached to a frame and configured providing excess covering material that is taken up upon remodeling and retraction.

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

As disclosed above, the present invention provides vascular valve devices that are configured with adaptations to take into account and/or reduce retraction of a covering material, especially a remodelable covering material that retracts upon remodeling with the patient's tissue. In this regard, the phenomenon of retraction when a material remodels generally involves the shrinkage or contraction of the material in one or multiple directions believed to be due to the action of cells invading and/or proliferating in or on the material. This retraction can lead to distortion of the implanted material and a variance between the shape and/or size of the implanted material and that of a remodeled structure containing the patient's tissue. Valve devices of the invention, adapted to account for and/or reduce the level of retraction of the implanted material, are useful for treating a variety of vascular diseases and, in particular embodiments of the invention, they are configured for implantation within a vein to treat venous insufficiency.

One embodiment of the invention provides a vascular valve device for implantation in a patient to form one or more leaflets of the patient's tissue in a target valve configuration. The valve device comprises a frame element and a remodelable covering material that retracts upon remodeling. The remodelable covering is attached to the frame element in a first configuration, e.g., for implantation, the first configuration having one or more leaflet-forming portions formed from the remodelable covering. The first configuration for implantation also includes an adaptation wherein upon remodeling of the leaflet-forming portions with the patient's tissue and retraction, one or more corresponding leaflets of the patient's tissue in a target valve configuration are formed. Target configurations for the valve devices of the invention may have varied geometries, and have as a common feature the ability to perform as a functional valve that facilitates an increase in the net blood flow in a given direction within a vascular vessel in which they are implanted. Desirable target valve configurations will include a closed condition having an area of leaflet coaptation (with one or more other leaflets in the case of a multi-leaflet valve, or with the vessel wall in the case of a mono-leaflet valve) that is sufficient to interrupt fluid communication through the valve orifice so as to restrict retrograde flow within the vascular vessel, for example by substantially or in preferred cases essentially completely interrupting fluid communication through the valve orifice in such closed condition. Desirable target valve configurations will include an open condition that permits blood flow through the valve orifice, with the leaflet(s) moving away from their coapting position to increase or re-establish fluid communication through the valve orifice. Advantageous target valve configurations will exhibit a valve opening area in the open-most position of the leaflets that represents a substantial percentage of the cross-sectional area of the vessel in which the prosthesis is implanted, for example at least about 60% or more desirably at least about 70%, to allow a substantially unrestricted flow of blood through the valve orifice when in its open condition.

In certain embodiments, the invention also provides vascular valve devices having a remodelable covering attached thereto which has been treated to reduce its tendency to retract upon remodeling. The valve device can comprise a frame element and a remodelable covering treated so as to reduce its retraction upon remodeling. The remodelable covering is attached to the frame element and provides one or more leaflets. Upon remodeling of the collagenous covering with the patient's tissue, one or more leaflets of the patient's tissue in the target valve configuration are formed.

In other aspects, the invention provides vascular valve devices that include both an adaptation to compensate for retraction and a treatment to reduce retraction of the remodelable covering.

A variety of covering material adaptations can be used in embodiments of the invention. For example, it has been discovered that retraction of the collagenous covering tends to occur to a greater extent along the orientation of fibers of a remodelable covering. Accordingly, one adaptation suitable for application comprises attaching the at least one sheet of remodelable covering to a frame element such that the fibers of the at least one sheet of remodelable covering are oriented substantially perpendicular to the longitudinal axis of the valve prosthesis, or parallel to the edge of the orifice of the valve. By having the fibers oriented in this fashion, retraction in a longitudinal direction, i.e. perpendicular to the valve orifice edge, is minimized.

Another adaptation suitable for application comprises attaching the remodelable covering to the frame element such that there is an excess of remodelable covering in the first or original configuration. This adaptation allows for a sufficient amount of remodeled material to be present once retraction occurs in order to exhibit the desired target configuration. An excess of remodelable covering can be included in a wide variety of orientations so as to achieve a remodeled leaflet or leaflets in the desired, functional target configuration. For example, the amount of covering provided parallel to and/or perpendicular to the longitudinal axis of the valve prosthesis can be such that there is slack or excess material as compared to the desired target configuration of the valve leaflet(s) after remodeling. Thus, in certain embodiments, in a first configuration for implantation, the leaflet(s) will be more rounded or billowed than is desired of the final target configuration, as provided by excess material in a direction perpendicular to the valve orifice. In practicing these aspects of the invention, the surface area of each of the one or more leaflets in the first configuration may exceed that of the target configuration by a significant amount, for example, at least about 5%, or at least about 10%. In addition, or alternatively, in certain embodiments, the coapting free edge or edges of the leaflet or leaflets in a first configuration will occur more downstream (in terms of the direction of blood flow) than is desired of the final target configuration. Upon retraction of the leaflet-forming material, the edge(s) will be pulled upstream to provide the valve orifice opening at the desired target location, e.g. substantially at a predetermined position relative to an element of the frame, e.g. substantially aligned with the downstream end of the frame. It will be understood that these and other strategies for incorporating extra material in the implantable configuration can be practiced within the scope of the present invention.

A further adaptation suitable for application in the invention comprises attaching multiple piece sheets of remodelable covering to the frame element, each providing the material for an individual leaflet. The multiple pieces are attached to the frame element such that portions of the pieces coapt. The multiple pieces of remodelable covering can be made of the same material and can be substantially the same size and shape. By having separate segments of remodelable material providing each leaflet, retraction of each leaflet can be accounted for individually, potentially also using other compensatory adaptations described herein.

Another adaptation suitable for application in the invention comprises treating the remodelable covering so as to reduce retraction of the covering upon remodeling. Treating for these purposes can involve a variety of alterations to a remodelable covering. For example, the treating can comprise stretching the covering material. In this manner, a covering material will be formed that has a larger surface area than it had previous to the pre-conditioning step. This may allow for the collagenous covering to retract back to or closer to its original dimensions once remodeling occurs with the patient's tissue.

The collagenous covering can also be subjected to low level crosslinking so as to reduce retraction but retain the capacity to effectively remodel. Crosslinking can, for example, be introduced by chemical treatment, such as glycation. The collagenous covering also can be subjected to a form of energy treatment to introduce crosslinking. For example, energy treatment suitable for use in the invention includes exposing the collagenous covering to ultraviolet light, to heat or both.

The treatment of the remodelable covering also can comprise coating and/or, impregnating the covering with a retraction-reducing agent. Suitable retraction-reducing agents may include, for example, agents that modulate cell growth or proliferation. These include, for instance, anti-proliferative agents, including microtubule stabilizing agents such as paclitaxel and analogs and derivatives thereof (see e.g., U.S. Pat. No. 5,616,608 for a discussion of such agents).

The adaptations described herein can be used alone or in combination to provide the desired effect of compensating for and/or reducing retraction of leaflets of a vascular valve device upon remodeling. As one example, it is contemplated to first pre-condition and/or treat the remodelable covering as described above, and then to attach the remodelable covering to a frame element such that the fibers of the remodelable covering are oriented parallel to the edge of a valve orifice and/or in a fashion that provides excess leaflet material that is taken up during remodeling.

Figure 2:
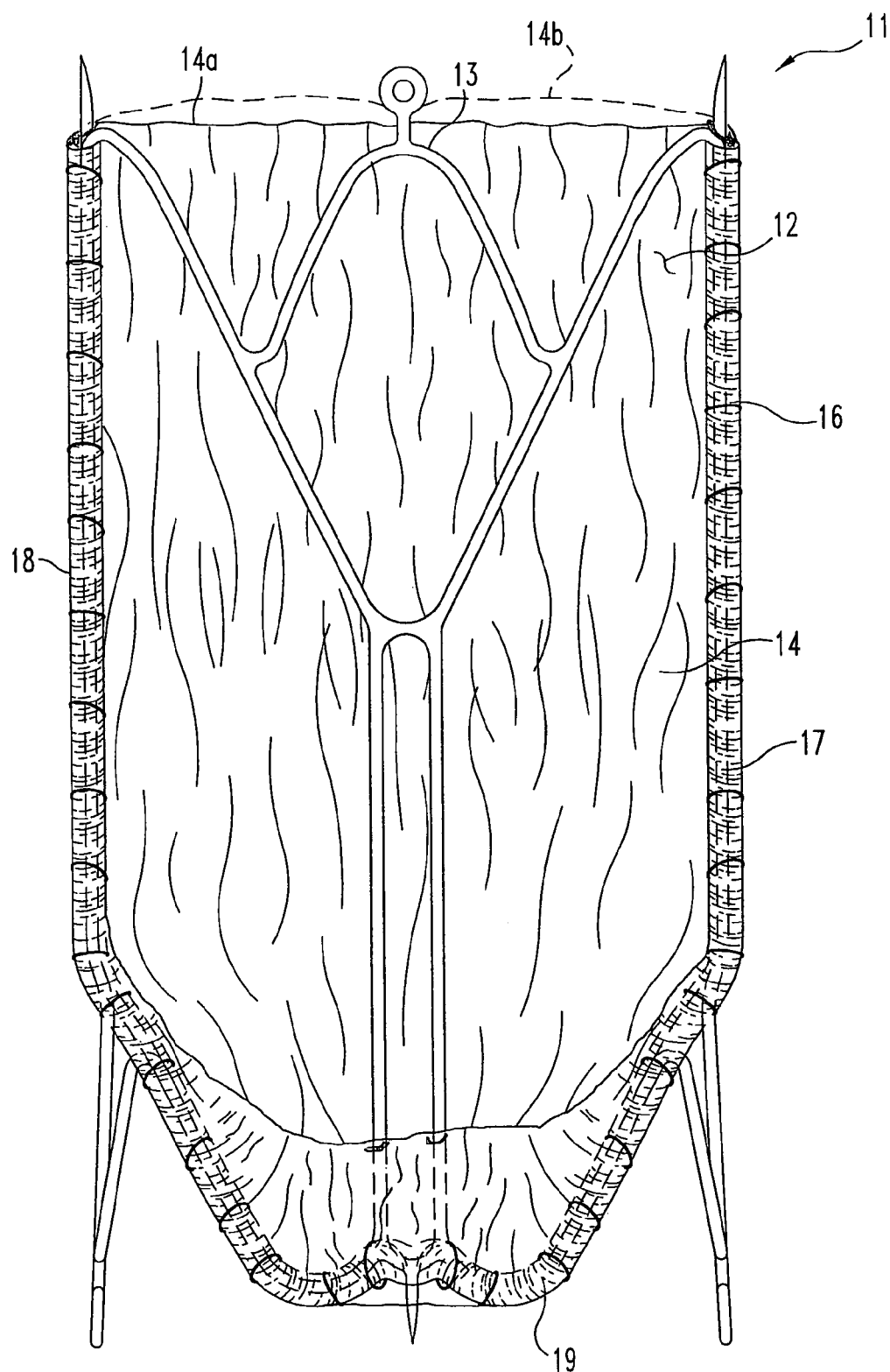
FIG. 2 provides a left side view of the illustrative vascular valve device depicted in FIG. 1.
Figure 3:
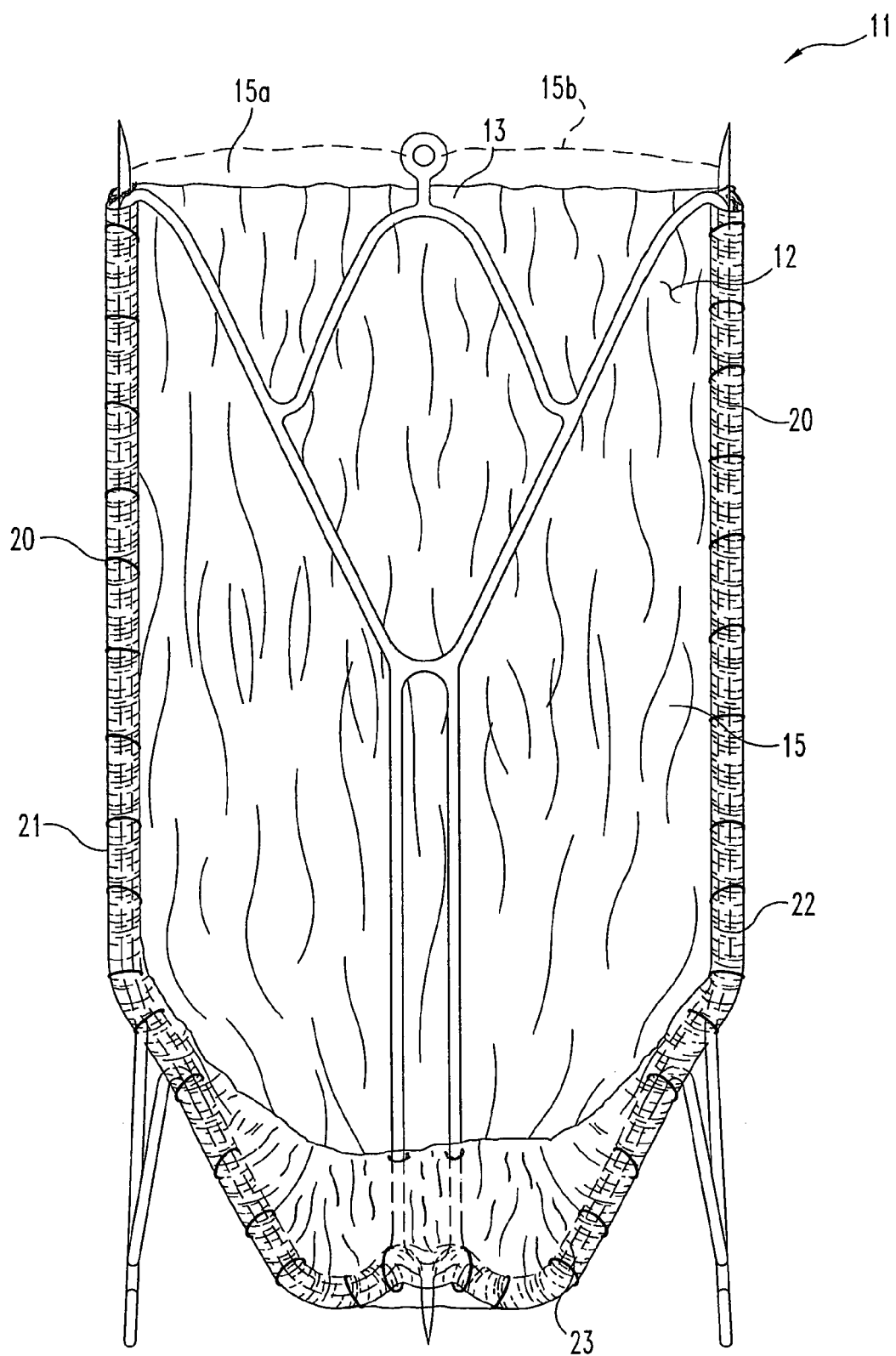
FIG. 3 provides a right side view of the illustrative vascular valve device depicted in FIG. 1.

With reference now to FIGS. 1-3, depicted are various side views of an illustrative vascular valve device 11 having a remodelable covering material 12 that retracts upon remodeling. The remodelable covering material 12 is attached to a frame element 13 and provides two leaflets 14 and 15 in an original configuration for implantation in a patient. In particular, FIG. 1 provides a side view of vascular valve device 11 viewed in a direction parallel to the coapting upper edges 14a and 15a of leaflets 14 and 15. FIG. 2 provides a view of the device 11 depicted in FIG. 1 taken from the left side. FIG. 3 provides a view of the device 11 depicted in FIG. 1 taken from the right side.

As can be seen from FIGS. 1-3, leaflets 14 and 15 include respective free edges 14a and 15a for coaptation with one another and respective fixed edges 16 and 20 that will each be forced against the wall of a vascular vessel upon implantation of device 11 in a path that partially circumscribes the vessel wall so as to each form a blood-capturing element. In the device 11 illustrated, the path of leaflet edge contact with the vessel wall includes substantial portions that extend essentially longitudinal along the vessel wall that connect to a cup-forming portion that extends both longitudinally along the vessel wall and circumferentially around the vessel wall. In particular, the fixed edge 16 of leaflet 14 includes opposite longitudinally-extending portions 17 and 18 each extending to an opposite side of a cup-forming portion 19. Correspondingly, the fixed edge 20 of leaflet 15 includes opposite longitudinally-extending portions 21 and 22 each extending to an opposite side of cup-forming portion 23.

Vascular valve device 11 includes an excess of the remodelable covering material 12 carried upon the frame element 13. The excess covering material may be provided in a direction transverse to (e.g. perpendicular to) and/or in a direction parallel to a longitudinal axis of the frame 13. This renders the leaflets 14 and 15 more slack than that which occurs in the target remodeled configuration in which the leaflets comprise tissue of the patient into which the valve device 11 is implanted. Thus, in the original or implanted configuration shown in FIGS. 1-3, the leaflets 14 and 15 may be generally more billowed in the open condition of the valve than in the target, remodeled configuration of the valve 11. In other ways to consider the excess covering material 12, the leaflets 14 and 15 may each present a greater leaflet surface area in the implanted configuration than in the target configuration, and/or from a cross-sectional standpoint, the leaflets 14 and 15 may define at least one cross-sectional path that is longer in the implanted configuration than in the target configuration.

In these regards, referring now to FIGS. 4I$^c$ and 4R$^c$, provided are overhead views of the vascular valve device 11 depicted in FIG. 1 in a closed position in the implanted (non-remodeled) configuration (11, FIG. 4I$^c$) and remodeled configuration (11', FIG. 4R$^c$). As can be seen in FIG. 4I$^c$, leaflets 14 and 15 as implanted coapt to provide a closed condition to the implanted valve 11 that restricts blood flow. Also, as shown in FIG. 4R$^c$, remodeled leaflets 14' and 15' coapt to provide a closed condition to the remodeled valve 11' that restricts blood flow. In the implanted valve configuration 11 shown in FIG. 4I$^c$, the path defined by the coapting portions of the implanted leaflets 14 and 15 is longer and significantly more tortuous than that defined by the remodeled leaflets 14' and 15' of the target configuration shown in FIG. 4R$^c$. This is due to the excess of covering material in the implanted configuration as compared to the target configuration, in a direction transverse (e.g. perpendicular) to the longitudinal axis of the frame 13. Thus, one feature of certain valve devices of the invention contemplates implanted valve configurations having longer and more tortuous coaptation paths than those of the corresponding target remodeled configuration. It will be understood that even in the remodeled configuration the coaptation path may be somewhat tortuous, or it may be substantially linear across the valve frame; however, it is anticipated that in the target configuration, any deviation from a substantially linear coaptation path will be reduced as compared to the implanted configuration.

With reference now to FIGS. 5I$^o$ and 5R$^o$, shown are overhead views of the vascular valve device 11 depicted in FIG. 1 in a closed position in the implanted (non-remodeled) configuration (11, FIG. 5I$^o$) and remodeled configuration (11', FIG. 5R$^o$). As shown in FIG. 5I$^o$, the implanted leaflets 14 and 15 are in the open condition, billowing outwardly from the centerline "C" of frame 13, thus creating a valve opening 30. For example, leaflets 14 and 15 extend a maximum distance D from the centerline C. Referring now to FIG. 5R$^o$, shown is the open condition of valve device 11' in the target configuration after remodeling with tissue of the patient. In this configuration, leaflets 14' and 15' extend a maximum distance D' from the centerline C that is less than the maximum distance D in the original implanted configuration (see FIG. 5I$^o$). Thus, also, valve opening 30' in the open-most condition of device 11' will be smaller than valve opening 30 in the openmost condition of device 11 in the original implanted configuration shown in FIG. 5I$^o$. In certain embodiments of the invention, the distance D in the original configuration for implant will be substantially greater than the distance D' in the remodeled configuration, for example at least about 0.5 mm greater. In addition or alternatively, the area defined by the valve opening in the implanted configuration will be substantially larger in the original configuration 30 for implant than in the remodeled configuration 30', for example at least about 5% larger, or at least about 10% larger. The area of the valve opening 30 in the configuration for implant when in its open-most condition may, for example, be from about 50% to 120% of the cross-sectional area of the vessel in which the valve prosthesis is implanted, more typically in the range of about 60% to about 100%. The corresponding valve opening area 30' of the remodeled configuration of the valve prosthesis in this embodiment will be substantially less than that of the original configuration for implant, and may, for example, be from about 40% to about 100% of the cross-sectional area of the vessel in which the device is to be implanted, more typically in the range of about 50% to about 95%. It will be understood that these represent certain embodiments and that other valve and leaflet configurations are encompassed by the broader aspects of the invention.

Turning now to a discussion of FIGS. 6I$^c$ and 6R$^c$ in combination with those discussed above, shown are cross-sectional views of leaflets 14,15 and 14',15' taken along lines 6I-6I and 6R-6R of FIGS. 4I$^c$ and 4R$^c$, respectively. These views are illustrative of the longitudinal cross-sections of the original and remodeled configurations of the valve leaflets. As illustrated by FIGS. 6I$^c$ and 6R$^c$, leaflets 14 and 15 of the implanted configuration may also have portions that billow more significantly than leaflets 14' and 15' of the remodeled configuration when considered in the longitudinal direction. Thus, when considering the excess covering material 12 in longitudinal cross-section, the leaflets 14 and 15 may define at least one cross-sectional path that is longer in the implanted configuration than in the target configuration, and may include at least one non-coapting portion along its length, e.g. as at line Z-Z in FIGS. 6I$^c$ and 6R$^c$, that billows or extends inwardly a distance d in a closed condition of the implanted configuration (FIG. 6I$^c$)) that is greater than a corresponding distance d' in a closed condition of the remodeled configuration (FIG. 6R$^c$).

In still further aspects, with continued reference to FIGS. 6I$^c$ and 6R$^c$, the maximum length of coaptation (LOC) of the leaflets 14 and 15 in the implanted configuration may be longer than that (LOC) in the target remodeled configuration, as shown, due to the retraction characteristic of the remodelable covering material from which the leaflets are formed. In this regard, in preferred devices such as device 11, the configuration of the leaflets will provide for their coaptation along a substantial portion (e.g. 10% or greater) of their length in both the implanted and target configurations. This significant length and consequent area of leaflet coaptation facilitates the accommodation of some variance in the amount of retraction exhibited by the leaflets during and/or after the remodeling process.

The amount of contacting or coapting leaflet area can be expressed in a number of different ways. The length of coaptation (e.g. LOC) in the original configuration for implant is desirably at least about 2 mm and may be as much as about 50 mm or more depending on the configuration of the valve prosthesis. In certain embodiments of the invention, the length of coaptation can be within the range of about 5 to about 30 mm, more typically about 5 to about 15 mm, in the original configuration for implant. The length of coaptation can represent a substantial percentage of the overall length of the valve prosthesis, for example at least about 5%, or at least about 10%, of the overall length of the prosthesis. In certain embodiments, the length of coaptation of the leaflets represents 10% to 80% of the length of the overall device, typically about 30% to about 60%, and more typically about 35% to about 55%.

In additional aspects of the invention, a long length of coaptation can be provided by orienting the outer leaflet edges substantially longitudinally along the frame in close proximity to one another over a significant distance. Thus, with reference to FIGS. 1-3 for purposes of illustration, outer leaflet edge portion 17 of leaflet 14 is configured to contact along the vessel wall in close proximity to outer leaflet edge portion 21 of leaflet 15 over a significant distance, for example 2 to 50 mm, typically about 5 to about 30 mm, and more typically about 5 to about 15 mm. The same would be true for the leaflet edge portions tracking along the opposite side of the vessel wall (e.g. edge portions 18 and 22, FIGS. 1-3). It is preferred that the leaflet edges remain in close proximity over these distances, for example within about 5 mm, more preferably within about 3 mm, and most preferably within about 1 mm. It will be understood that this close proximity may involve having the leaflet edges track closely with one another along the vessel wall, or may have them being attached along essentially the same path (e.g. both along a single strut of a frame) and thus exhibiting essentially no separation from one another as they pass along the vessel wall.

Figure 7:
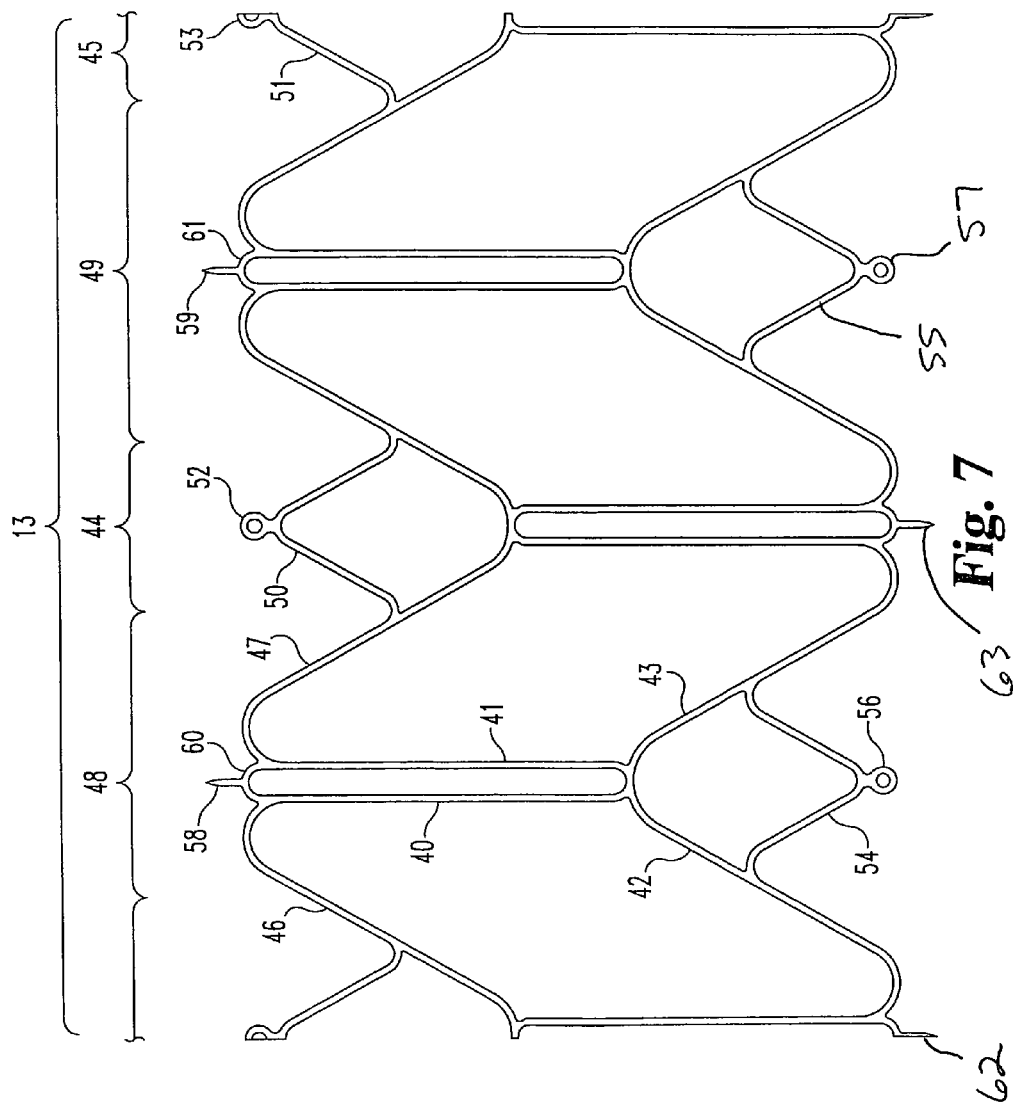
FIG. 7 provides a planarized view illustrating the strut pattern of the frame of the illustrative devices depicted in FIGS. 1-4.

With reference now to FIGS. 1-6R$^c$ together with FIG. 7, which presents a planar depiction showing the strut patterns of the frame 13, additional details regarding the frame 13 will be discussed. Frame 13 includes longitudinal attachment struts 40,41 that are generally aligned with the longitudinal axis of the valve prosthesis 11 and distal strut 42,43 portions that extend laterally outward from the longitudinal attachment struts 40,41. Distal strut portion 42 together with strut portion 43 converge at a point oppositely facing each leaflet 14,15 where they attach to a lateral support structure 44,45. The support frame 13 also includes proximal support arms 46 and 47 that attach to and extend from the longitudinal attachment struts 40,41 and provide an interconnection with the lateral support structure 44,45. As can be seen, the lateral support structure 44,45 mirrors the configuration of the longitudinal attachment strut regions 48,49 that they interconnect, except that they are located 90° therefrom and oriented oppositely thereto, such that the frame generally includes a serpentine configuration adapted to be readily collapsible and expandable. The repeating, uniform design of the frame 13 of the illustrative embodiment advantageously provides better structural stability, compressibility/expandability, and overall integrity than a support structure that comprises a non-uniform, non-repeating frame pattern.

The lateral arms 46,47 each connect to a strut 50,51 that carries a proximal radiopaque marker 52,53 that can be used to facilitate orientation and location of the device 11 and provide additional support. Identical distal struts 54,55 are located distal to the longitudinal attachment struts 40,41 and an optional radiopaque marker 56,57 is provided on each. Integral barbs 58,59 are located at the proximal end of device 11 on the bends 60,61 that connect the longitudinal attachment struts 40,41. Corresponding integral barbs 62,63 are located at the distal end of device 11. Barbs 58,59,62,63 facilitate anchoring the device 11 in place in the vascular vessel by penetration into the vascular wall.

Figure 8:
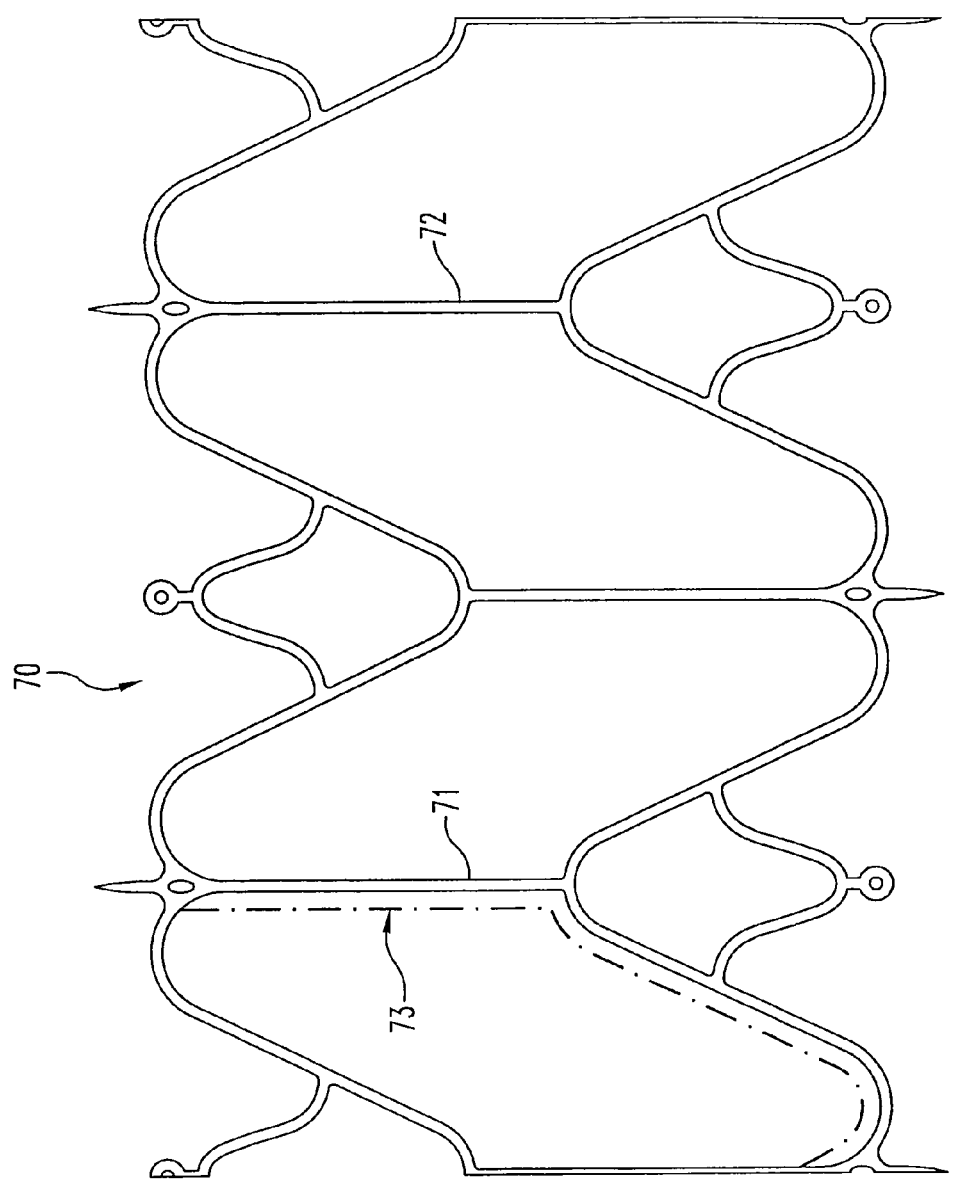
FIG. 8 provides a planarized view illustrating an alternate strut pattern for a frame that can be used to prepare illustrative valve prostheses.

FIG. 8 depicts a similar frame 70 to that depicted in FIGS. 1-6R$^c$ except including single longitudinal attachment struts 71,72. The edges of the leaflets (such as 14,15) can be similarly attached along the single attachment struts 71,72 to provide a long length of coaptation (see illustrative leaflet edge path 73 shown by dotted line). For example, the leaflet edges can be attached such that each abuts the strut 71,72 (and sewn or attached without being wrapped over the strut) or the first lateral leaflet edge can be wrapped around the strut 71,72 while the second lateral leaflet edge of the opposite leaflet is sewn or otherwise attached over the first lateral leaflet edge and strut. Further, thicker struts 71,72 could include apertures or slots of any shape or length distributed therealong for receiving sutures or other attachment elements such as clips, rings, etc., for affixing or anchoring the leaflet outer edges thereto.

When implanted in a vascular lumen such as a vein, the feature of excess covering material in the lateral direction may lead to a number of conditions of the valve in use. For example, where the target configuration is to have the open condition of the valve include the leaflets fully pressed against the vessel wall, the leaflets in the implanted configuration may include wrinkles or folds when the valve is in the open condition, but upon remodeling and retraction of the covering material, these wrinkles or folds will lessen or be eliminated providing the desired final target configuration. On the other hand, where the target configuration of the valve in the open condition will include the leaflets spaced somewhat inwardly from the vessel wall (i.e., not pressed entirely against the walls), the original implanted configuration with excess slack material may result in a wrinkled or folded condition prior to retraction as discussed above, or a relatively smooth condition in which the leaflets are pressed against the wall, or a condition in which the leaflets are not pressed against the wall, in particular, at their upper coapting edges but extend outwardly and provide a valve opening larger than the leaflets in the corresponding remodeled, final condition. Each of these variations is contemplated as being within the spirit and scope of the present invention.

In accordance with the invention, an excess of remodelable covering material can be provided in a longitudinal direction on the frame in order to account and compensate for longitudinal retraction of the covering material upon remodeling. Specifically, a vascular valve device can include one or more leaflets mounted upon a frame, wherein the original configuration of the leaflets provides an excess amount of remodelable covering material in the longitudinal direction along the frame. Again, this can render the leaflets more billowed when considered in longitudinal cross-section than they will appear in the final, remodeled configuration. This can result in various characteristics of the valve material upon implantation and prior to remodeling. For example, the leaflets may press against the vein or other vascular lumen wall over a greater surface area in the original implanted configuration as opposed to the retracted remodeled configuration. In addition, the material of the leaflets may form folds or wrinkles where pressed against the lumen wall.

Still further, in accordance with another aspect of the invention, an excess of remodelable covering material can be provided at the upper, coapting edges of the leaflets. Illustratively, a section of leaflet material having an arcuate moving/coapting edge can be provided to the leaflets, as illustrated by dotted lines 14*b* and 15*b* in FIGS. 2 and 3, respectively. As illustrated, the excess material can extend above the uppermost point of attachment of the leaflet material to frame 13 in the implanted configuration, but upon retraction the upper edges of leaflets can then be pulled downwardly, e.g. to become substantially co-planar with the uppermost point of attachment of the leaflets to the frame. These and other configurations providing an overhanging segment that is reduced or eliminated upon retraction of the remodelable material are contemplated as being a part of the present invention.

Figure 9:
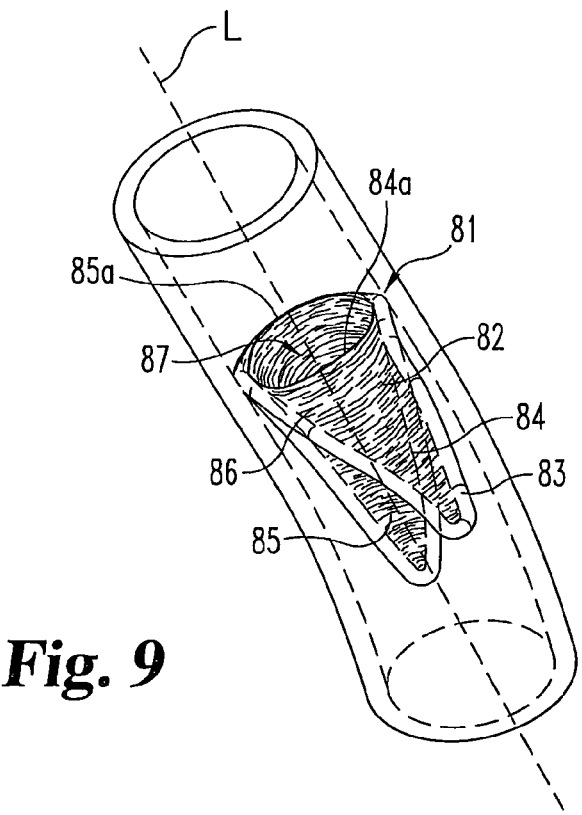
FIG. 9 provides a perspective view of an illustrative vascular valve device including a remodelable covering attached to a frame such that fibers of the remodelable covering are oriented parallel to the valve orifice.

With reference now to FIG. 9, illustrated is an embodiment of the invention comprising a vascular valve device 81 including a remodelable covering material 82 attached to a frame element 83 and configured to form leaflets 84 and 85. In this embodiment, the remodelable covering material 82 includes directionally-oriented fibers 86, and the covering material exhibits a lower level of retraction in the direction of the fibers 86 upon remodeling. In the illustrated device 81, the direction of the fibers 86 is oriented substantially transverse to, such as perpendicular to, the longitudinal axis L of the device 81. This orients the fibers 86 substantially parallel to the movable upper edges 84*a* and 85*a* of the leaflets 84 and 85 forming the valve orifice 87. In this manner, retraction of the covering material in a direction transverse to (e.g., perpendicular to) the direction of the valve orifice will be reduced as compared to retraction in a direction parallel to the orifice.

Figure 10:
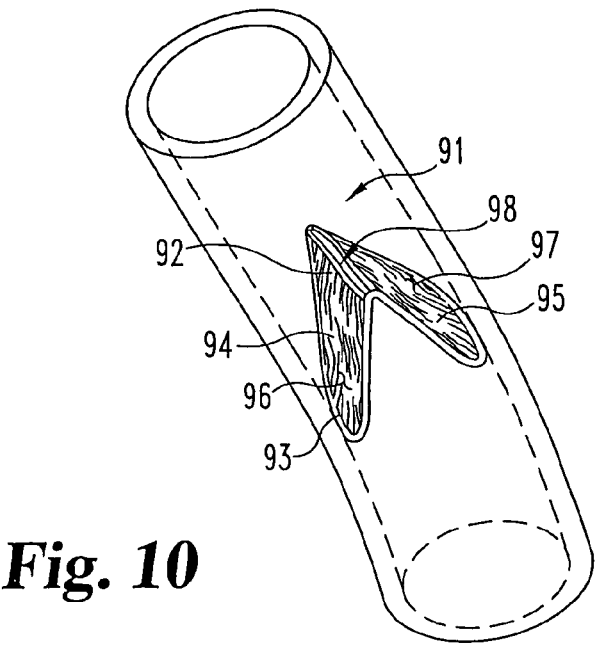
FIG. 10 provides a perspective view of an illustrative vascular valve device including two separate sheets of remodelable covering attached to a frame element.

With reference now to FIG. 10, shown is a vascular valve device of the invention 91 including covering material 92 (in two separate pieces) attached to a frame element 93. The covering material 92 forms leaflets 94 and 95, with each separate piece of covering material 92 forming an individual leaflet. In particular, a first piece of remodelable covering material 96 is attached to a portion of frame element 93 and a second piece of covering material 97 is attached to a different portion of frame element 93. The first piece 96 and second piece 97 of remodelable covering form respective leaflets 94 and 95 which include portions that coapt in the central region of the frame element 93 to form a valve orifice 98. In this manner, potential stresses caused by retraction are isolated between the separate pieces of covering material. This can allow better or more facile compensation for retraction. Illustratively, when using a single piece of covering material having a centrally-located slit to provide the valve orifice, stresses can be created at the outer edges of the slit due to retraction of the covering material in the adjacent outwardly-lying areas.

The remodelable covering for use in a vascular valve device of the invention can be comprised of a naturally-derived or synthetic material. Preferably, the remodelable covering is collagenous, and in more preferred embodiments it comprises an extracellular matrix material (ECM). Suitable extracellular matrix materials include, for instance, submucosa (including for example small intestinal submucosa, stomach submucosa, urinary bladder submucosa, or uterine submucosa), tissue mucosa, renal capsule membrane, dura mater, pericardium, serosa, peritoneum or basement membrane materials, including liver basement membrane. Preferably, the ECM comprises small intestinal submucosa (SIS). These layers may be isolated and used as intact natural sheet forms, or reconstituted collagen layers including collagen derived from these materials or other collagenous materials may be used. For additional information as to submucosa materials useful in the present invention, and their isolation and treatment, reference can be made to U.S. Pat. Nos. 4,902, 508, 5,554,389, 5,993,844, 6,206,931, and 6,099,567.

As prepared and used, the submucosa material or any other ECM material may optionally retain growth factors or other bioactive components native to the source tissue. For example, the submucosa or other ECM material may retain one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in certain embodiments of the invention may retain other biological materials such as heparin, heparin sulfate, hyaluronic acid, fibronectin and the like. Thus, generally speaking, the submucosa or other ECM material may retain a bioactive component that induces, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of such native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a premanufactured step, immediately prior to application (e.g. by soaking the material in a solution containing a suitable antibiotic such as cefazolin), or during or after application of the ECM material to the patient.

Submucosa or other ECM material used in certain embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in certain embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa used in certain embodiments of the present invention.

Frame elements of the present invention may also be made from any suitable biocompatible material. These include, for example, numerous base materials such as biocompatible metals or other metallic materials; polymers including bioabsorbable or biostable polymers; stainless steels (e.g., 316, 316L or 304); nickel-titanium alloys including shape memory or superelastic types (e.g., nitinol or elastinite); noble metals including platinum, gold or palladium; refractory metals including tantalum, tungsten, molybdenum or rhenium; stainless steels alloyed with noble and/or refractory metals; silver; rhodium; inconel; iridium; niobium; titanium; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; nonmetallic biocompatible materials including polyamides, polyolefins (e.g., polypropylene or polyethylene), nonabsorbable polyesters (e.g., polyethylene terephthalate) or bioabsorbable aliphatic polyesters (e.g., homopolymers or copolymers of lactic acid, glycolic acid, lactide, glycolide, para-dioxanone, trimethylene carbonate or .epsilon.-caprolactone); polymeric materials (e.g., poly-L-lactic acid, polycarbonate, polyethylene terephthalate or engineering plastics such as thermotropic liquid crystal polymers (LCPs)); biocompatible polymeric materials (e.g., cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene or polytetrafluoroethylene); degradable or biodegradable polymers, plastics, natural (e.g., animal, plant or microbial) or recombinant material (e.g., polylactic acid, polyglycolic acid, polyanhydride, polycaprolactone, polyhydroxybutyrate valerate, polydepsipeptides, nylon copolymides, conventional poly(amino acid) synthetic polymers, pseudo-poly (amino acids) or aliphatic polyesters (e.g., polyglycolic acid (PGA), polylactic acid (PLA), polyalkylene succinates, polyhydroxybutyrate (PHB), polybutylene diglycolate, poly epsilon-caprolactone (PCL), polydihydropyrans, polyphosphazenes, polyorthoesters, polycyanoacrylates, polyanhydrides, polyketals, polyacetals, poly(.alpha.-hydroxy-esters), poly(carbonates), poly(imino-carbonates), poly(.beta.-hydroxy-esters) or polypeptides)); polyethylene terephthalate (e.g., dacron or mylar); expanded fluoropolymers (e.g., polytetrafluoroethylene (PTFE)); fluorinated ethylene propylene (FEP); copolymers of tetrafluoroethylene (TFE) and per fluoro(propyl vinyl ether) (PFA)); homopolymers of polychlorotrifluoroethylene (PCTFE) and copolymers with TFE; ethylene-chlorotrifluoroethylene (ECTFE); copolymers of ethylene-tetrafluoroethylene (ETFE); polyvinylidene fluoride (PVDF); polyvinyfluoride (PVF); polyaramids (e.g., kevlar); polyfluorocarbons including polytetrafluoroethylene with and without copolymerized hexafluoropropylene (e.g., teflon or goretex); expanded fluorocarbon polymers; polyglycolides; polylactides; polyglycerol sebacate; polyethylene oxide; polybutylene terepthalate; polydioxanones; proteoglycans; glycosaminoglycans; poly (alkylene oxalates); polyalkanotes; polyamides; polyaspartimic acid; polyglutarunic acid polymer; poly-p-diaxanone (e.g., PDS); polyphosphazene; polyurethane including porous or nonporous polyurethanes; poly(glycolide-trimethylene carbonate); terpolymer (copolymers of glycolide, lactide or dimethyltrimethylene carbonate); polyhydroxyalkanoates (PHA); polyhydroxybutyrate (PHB) or poly (hydroxybutyrate-co-valerate) (PHB-co-HV); poly(epsilon-caprolactone) (e.g., lactide or glycolide); poly(epsilon-caprolactone-dimethyltrimethylene carbonate); polyglycolic acid (PGA); poly-L and poly-D(lactic acid) (e.g., calcium phosphate glass); lactic acid/ethylene glycol copolymers; polyarylates (L-tyrosine-derived) or free acid polyarylates; polycarbonates (tyrosine or L-tyrosine-derived); poly(esteramides); poly(propylene fumarate-co-ethylene glycol) copolymer (e.g., fumarate anhydrides); polyanhydride esters; polyanhydrides; polyorthoesters; prolastin or silk-elastin polymers (SELP); calcium phosphate (bioglass); compositions of PLA, PCL, PGA ester; polyphosphazenes; polyamino acids; polysaccharides; polyhydroxyalkanoate polymers; various plastic materials; teflon; nylon; block polymers or copolymers; Leica RM2165; Leica RM2155; organic fabrics; biologic agents (e.g., protein, extracellular matrix component, collagen, fibrin); small intestinal submucosa (SIS)RP (e.g., vacuum formed SIS); collagen or collagen matrices with growth modulators; aliginate; cellulose and ester; dextran; elastin; fibrin; gelatin; hyaluronic acid; hydroxyapatite; polypeptides; proteins; ceramics (e.g., silicon nitride, silicon carbide, zirconia or alumina); bioactive silica-based materials; carbon or carbon fiber; cotton; silk; spider silk; chitin; chitosan (NOCC or NOOC-G); urethanes; glass; silica; sapphire; composites; any mixture, blend, alloy, copolymer or combination of any of these; or various other materials not limited by these examples. Preferably, the frame element comprises a superelastic metal alloy material.

The valve devices of the invention are desirably vascular valves adapted for deployment within the vascular system and, in particularly preferred embodiments, vascular valve devices of the invention are adapted for deployment within the venous system. Accordingly, preferred valve devices, such as valve devices 11, 81 and 91 are adapted as a venous valve, for example, for implantation within superficial or deep veins of the legs or feet, to treat venous insufficiency and/or varicose vein syndrome.

Valve devices of the invention can include therapeutic or otherwise beneficial agents coating and/or incorporated within the remodelable covering material and/or the frame element. As examples, valve devices of the invention may include heparin and/or another anticoagulant substance coating and/or impregnated within the remodelable covering material.

Vascular valve devices of the invention can be adapted to provide a monocusp valve in a vein or artery or, alternatively, it can be adapted to provide for a multicuspid valve in a vein or artery, wherein the multicuspid valve comprises a plurality of cusps (i.e. two or more). In this respect, certain vascular valve devices can be adapted to provide a monocuspid valve, a bicuspid valve, a tricuspid valve, or a quadracuspid valve.

When a monocusp leaflet configuration is utilized in the invention, the vascular valve device having such a configuration will be attached in such a manner so as to allow the leaflet to extend across the lumen of a vein sufficiently to restrict blood flow in a selected direction and desirably to co-apt with the opposite wall of the vein. When a multicusp leaflet configuration is utilized, the vascular valve device will comprise leaflets configured in such a manner to allow the leaflets to co-apt within the lumen of the vessel.

Also provided are medical products that include illustrative vascular valve devices of the invention sealed within medical packaging. Kits may also be provided including such products potentially in combination with other components, for example, including one or more of a sheath, catheter, or guidewire. The final, packaged products are provided in sterile condition. This may be achieved, for example, by gamma, e-beam or other irradiation techniques, ethylene oxide gas, or any other suitable sterilization technique, and the materials and other properties of the medical packaging will be selected accordingly. The vascular devices may be packaged wet or after they are dry.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are indicative of the abilities of those of ordinary skill in the art and are hereby incorporated by reference in their entirety as if individually incorporated by reference and fully set forth.

What is claimed is:

1. A vascular valve device for implantation in a patient to form two or more leaflets including tissue of the patient in a target configuration, the valve device comprising:
   a frame having a longitudinal axis;
   a remodelable covering that retracts upon remodeling, the remodelable covering attached to the frame in a first configuration for implantation, the first configuration having two or more leaflet-forming portions formed from the remodelable covering;
   said first configuration adapted wherein upon a remodeling of the two or more leaflet-forming portions and consequent retraction, two or more leaflets comprising tissue of the patient in the target valve configuration are formed;
   wherein said first configuration for implantation provides a first coaptation path along which the two or more leaflet-forming portions coapt in a closed condition of the valve device, said first coaptation path extending transverse to the longitudinal axis of the frame, and wherein an excess of the remodelable covering provided in a direction transverse to the longitudinal axis of said frame causes said first coaptation path to be tortuous;

wherein said target configuration provides a target coaptation path along which the two or more leaflets coapt in a closed condition of the valve device, said target coaptation path extending transverse to the longitudinal axis of the frame, and wherein said target coaptation path is less tortuous than said first coaptation path due to remodeling and consequent retraction of said leaflet-forming portions of said remodelable covering.

2. The vascular valve device of claim 1, wherein the remodelable covering is attached to the frame such that fibers of the remodelable covering are oriented substantially parallel to a valve orifice created by the one or more leaflets.

3. The vascular valve device of claim 1, wherein each leaflet-forming portion comprises a separate piece of said remodelable covering.

4. The vascular valve device of claim 1, wherein the remodelable covering has been pre-conditioned by stretching.

5. The vascular valve device of claim 1, wherein an excess of remodelable covering is also provided at least in a direction substantially parallel to the longitudinal axis of the frame.

6. The vascular valve device of claim 1, wherein an excess of remodelable covering is also provided at least in a direction substantially perpendicular to the valve orifice.

7. The vascular valve device of claim 1, wherein the remodelable covering is treated with an agent that reduces retraction of the covering upon remodeling.

8. The vascular valve device of claim 7, wherein the remodelable covering is treated with a crosslinking agent.

9. The vascular valve device of claim 8, wherein the remodelable covering is crosslinked by glycation.

10. The vascular valve device of claim 7, wherein the remodelable covering is crosslinked by subjecting the covering to energy.

11. The vascular valve device of claim 10, wherein the energy is provided by subjecting the covering to ultraviolet light.

12. The vascular valve device of claim 10, wherein the energy is provided by subjecting the covering to heat.

13. The vascular valve device of claim 7, wherein the remodelable covering is treated with an anti-proliferative agent.

14. The vascular valve device of claim 13, wherein the anti-proliferative agent comprises Paclitaxel.

15. The vascular valve device of claim 13, wherein the anti-proliferative agent comprises a microtubule-inhibiting agent.

16. The vascular valve device of claim 1, wherein the remodelable covering comprises a collagenous extracellular matrix (ECM)

17. The vascular valve device of claim 16, wherein the ECM comprises a member selected from the group consisting of pericardium, submucosa, basement membrane, and dura mater.

18. The vascular valve device of claim 17, wherein the ECM comprises submucosa.

19. The vascular valve device of claim 1, wherein the frame comprises a wire structure.

20. The vascular valve device of claim 1, wherein the frame comprises a superelastic material.

21. A vascular valve device for implantation in a patient to form one or more leaflets comprising tissue of the patient, the valve device comprising a remodelable material treated with an agent to reduce retraction of the material upon remodeling and configured to provide one or more leaflet-forming portions that effectively remodel with tissue of the patient to form one or more corresponding leaflets comprising tissue of the patient;

wherein said agent comprises an anti-proliferative agent and the remodelable material is treated by coating the remodelable material with the agent; and wherein said anti-proliferative agent comprises a microtubule inhibiting agent.

22. The vascular valve device of claim 21, wherein said agent comprises Paclitaxel.

23. The vascular valve device of claim 21, wherein the remodelable material comprises an extracellular matrix (ECM).

24. The vascular valve device of claim 23, wherein the ECM comprises a member selected from the group consisting of pericardium, submucosa, basement membrane, and dura mater.

25. The vascular valve device of claim 24, wherein the ECM comprises submucosa.

26. The vascular valve device of claim 21, wherein the vascular valve device includes a frame to which said one or more leaflet-forming portions are attached.

27. The vascular valve device of claim 26, wherein the frame comprises a superelastic material.

28. A method of preparing a vascular valve device for implantation in a patient, comprising:

providing a frame having a longitudinal axis;

attaching to the frame a remodelable covering material in a first valve configuration having two or more leaflet-forming portions, wherein the remodelable covering material retracts upon remodeling;

said first valve configuration adapted wherein upon implantation of the device and remodeling of the covering material with the patient's tissue and consequent retraction, two or more leaflets comprising tissue of the patient in a target valve configuration are formed from the leaflet-forming portions;

wherein said first valve configuration provides a first coaptation path along which the two or more leaflet-forming portions coapt in a closed condition of the valve device, said first coaptation path extending transverse to the longitudinal axis of the frame, and wherein an excess of the remodelable covering provided in a direction transverse to the longitudinal axis of said frame causes said first coaptation path to be tortuous;

wherein said target configuration provides a target coaptation path along which the two or more leaflets coapt in a closed condition of the valve device, said target coaptation path extending transverse to the longitudinal axis of the frame, and wherein said target coaptation path is less tortuous than said first coaptation path due to remodeling and consequent retraction of said leaflet-forming portions of said remodelable covering material.

29. A vascular valve device for implantation in a patient to form multiple leaflets including tissue of the patient in a target configuration, the valve device comprising:

a frame;

a remodelable covering that retracts upon remodeling, the remodelable covering attached to the frame in a first configuration for implantation, the first configuration having multiple leaflet-forming portions formed from the remodelable covering;

said first configuration adapted wherein upon remodeling of the multiple leaflet-forming portions and consequent retraction, multiple leaflets comprising tissue of the patient in the target valve configuration are formed; and wherein each said leaflet-forming portion comprises a separate piece of said remodelable covering.

30. The vascular valve device of claim 29, wherein the remodelable covering comprises an extracellular matrix (ECM).

31. The vascular valve device of claim 30, wherein the ECM comprises a member selected from the group consisting of pericardium, submucosa, basement membrane, and dura mater.

32. The vascular valve device of claim 31, wherein the ECM comprises submucosa.

33. A vascular valve device for implantation in a patient to form one or more leaflets including tissue of the patient in a target configuration, the valve device comprising:

a frame;

a remodelable covering that retracts upon remodeling, the remodelable covering attached to the frame in a first configuration for implantation, the first configuration having one or more leaflet-forming portions formed from the remodelable covering;

said first configuration adapted wherein upon remodeling of the one or more leaflet-forming portions and consequent retraction, one or more leaflets comprising tissue of the patient in the target valve configuration are formed;

wherein said remodelable covering is treated with an agent that reduces retraction of the covering upon remodeling, wherein said agent is a crosslinking agent, and wherein said crosslinking agent causes said remodelable covering to be crosslinked by glycation.

* * * * *

UNITED STATES PATENT AND TRADEMARK OFFICE
Certificate

Patent No. 7,458,987 B2                                                                Patented: December 2, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Brian C. Case, Bloomington, IN (US); Jacob A. Flagle, Indianapolis, IN (US); Michael L. Garrison, Indianapolis, IN (US); F. Joseph Obermiller, West Lafayette, IN (US); Dusan Pavcnik, Portland, OR (US); and Michael C. Hiles, West Lafayette, IN (US).

Signed and Sealed this Twentieth day of April 2010.

CORRINE M. MCDERMOTT
                                                                                                  *Supervisory Patent Examiner*
                                                                                                        Art Unit 3738